(12) United States Patent
Puleo et al.

(10) Patent No.: US 12,697,092 B2
(45) Date of Patent: Aug. 4, 2026

(54) NEUROMODULATION ENERGY APPLICATION TECHNIQUES

(71) Applicant: GE Precision Healthcare LLC, Waukesha, WI (US)

(72) Inventors: Christopher Michael Puleo, Niskayuna, NY (US); Jeffrey Michael Ashe, Gloversville, NY (US); David Andrew Shoudy, Niskayuna, NY (US); Victoria Eugenia Cotero, Troy, NY (US); James Enrico Sabatini, Glenville, NY (US)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/623,858

(22) Filed: Apr. 1, 2024

(65) Prior Publication Data

US 2024/0237966 A1     Jul. 18, 2024

Related U.S. Application Data

(62) Division of application No. 16/517,289, filed on Jul. 19, 2019, now Pat. No. 11,944,490.

(51) Int. Cl.
*A61B 8/00*          (2006.01)
*A61N 7/00*          (2006.01)

(52) U.S. Cl.
CPC .......... *A61B 8/4236* (2013.01); *A61B 8/4281* (2013.01); *A61N 7/00* (2013.01); *A61N 2007/0026* (2013.01)

(58) Field of Classification Search
CPC ...... A61N 7/00; A61B 8/4281; A61B 8/4236; A61B 8/4477; A61B 8/4209
See application file for complete search history.

(56) References Cited

U.S. PATENT DOCUMENTS

| | | | | |
|---|---|---|---|---|
| 4,920,966 A | * | 5/1990 | Hon ..................... | A61B 8/4236 |
| | | | | 600/459 |
| 2005/0240126 A1 | * | 10/2005 | Foley ....................... | A61B 8/06 |
| | | | | 601/2 |
| 2015/0135840 A1 | * | 5/2015 | Sato ....................... | G01N 29/28 |
| | | | | 73/644 |
| 2017/0296295 A1 | * | 10/2017 | Wagner .................. | A61B 90/39 |
| 2018/0028841 A1 | * | 2/2018 | Konofagou ............ | A61B 8/085 |
| 2018/0263597 A1 | * | 9/2018 | Tchang .................. | A61B 90/50 |
| 2022/0361844 A1 | * | 11/2022 | Shoudy ................ | A61B 8/4477 |

* cited by examiner

*Primary Examiner* — Anh Tuan T Nguyen
*Assistant Examiner* — Younhee Choi
(74) *Attorney, Agent, or Firm* — Fletcher Yoder P.C.

(57) ABSTRACT

Provided herein are techniques directed to accurate positioning of an energy application device for neuromodulation treatment protocols. In one embodiment, a neuromodulation positioning patch is applied to a patient's skin. The energy application device is coupled to a frame of the neuromodulation positioning patch to position a transducer of the energy application device within an opening at a treatment position within the opening. In one embodiment, the frame is also coupled to a removable dock for an imaging probe that, when coupled to the removable dock and, in turn, the frame of the neuromodulation positioning patch, acquires image data through the opening to identify or verify a treatment position.

15 Claims, 9 Drawing Sheets

95

96

34

NEUROMODULATION ENERGY APPLICATION TECHNIQUES

CROSS-REFERENCE TO RELATED APPLICATIONS

The present application is a divisional application of U.S. patent application Ser. No. 16/517,289, filed on Jul. 19, 2019, the specification of which is incorporated by reference in its entirety.

BACKGROUND

The subject matter disclosed herein relates to techniques to support application of neuromodulating energy doses in a subject via application of neuromodulating energy to cause targeted physiological outcomes. In particular, the disclosed techniques may be part of a repeated dose protocol, a self-application protocol, and/or an at-home neuromodulation treatment protocol.

Neuromodulation has been used to treat a variety of clinical conditions. For example, electrical stimulation at various locations along the spinal cord has been used to treat chronic back pain. However, positioning electrodes at or near the target nerves is challenging. For example, such techniques may involve surgical placement of the electrodes that deliver the energy. In addition, specific tissue targeting via neuromodulation is challenging. Electrodes that are positioned at or near certain target nerves mediate neuromodulation by triggering an action potential in the nerve fibers, which in turn results in neurotransmitter release at a nerve synapse and synaptic communication with the next nerve. Such propagation may result in a relatively larger or more diffuse physiological effect than desired, as current implementation of implanted electrodes stimulate many nerves or axons at once. Because the neural pathways are complex and interconnected, a more selective and targeted modulated effect may be more clinically useful. However, the effectiveness of selective targeting specific neural may be dependent on accurate positioning of the energy application device.

BRIEF DESCRIPTION

Certain embodiments commensurate in scope with the claimed subject matter are summarized below. These embodiments are not intended to limit the scope of the claimed subject matter, but rather these embodiments are intended only to provide a brief summary of possible embodiments. Indeed, the disclosure may encompass a variety of forms that may be similar to or different from the embodiments set forth below.

In one embodiment, neuromodulation energy application system is provided that includes a neuromodulation positioning patch. The neuromodulation positioning patch includes a conformable substrate comprising an application surface configured to be applied to a subject's skin, the application surface comprising an adhesive portion, wherein the conformable substrate forms a first opening that permits viewing of a portion of the subject's skin through the first opening when the conformable substrate is applied. The neuromodulation positioning patch also includes a resilient frame disposed on the conformable layer to frame the first opening and protruding from a top surface of the conformable layer, the top surface opposing the adhesive surface. The neuromodulation positioning patch also includes a dock configured to removably mate with the resilient frame, wherein the dock forms a shaped passage that terminates in a second opening, wherein the second opening sits within the first opening when the dock is mated with the resilient frame. The neuromodulation energy application system also includes an ultrasound therapy probe configured to fit within or couple to the frame to apply neuromodulating energy through the portion of the subject's skin to a region of interest of an internal tissue.

In another embodiment, a method is provided that includes the steps of acquiring image data of a subject; identifying or verifying a region of interest based on the acquired image data; determining a treatment position on the skin of the subject based on the region of interest; positioning a neuromodulation positioning patch on the skin of the subject such that an opening formed in the neuromodulation positioning patch is positioned on or over the treatment position; coupling an ultrasound therapy probe to the neuromodulation positioning patch to position a therapy transducer of the ultrasound therapy probe through the opening and at the treatment position; and applying ultrasound energy from the ultrasound therapy probe through the treatment position to the region of interest treatment position.

In another embodiment, a neuromodulation positioning patch is provided that includes a conformable substrate comprising an opening extending through the conformable substrate; an adhesive disposed on an application surface of the conformable substrate; a resilient frame coupled to the substrate about a perimeter of the opening and protruding from a top surface of the conformable substrate, the resilient frame comprising one or more mating features; and at least one dock for an ultrasound imaging probe configured to removably mate with the resilient frame via one or more complementary mating features to the one or more mating features, wherein the dock forms a shaped passage that terminates in a second opening, wherein the second opening sits within the first opening when the dock is mated with the resilient frame.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
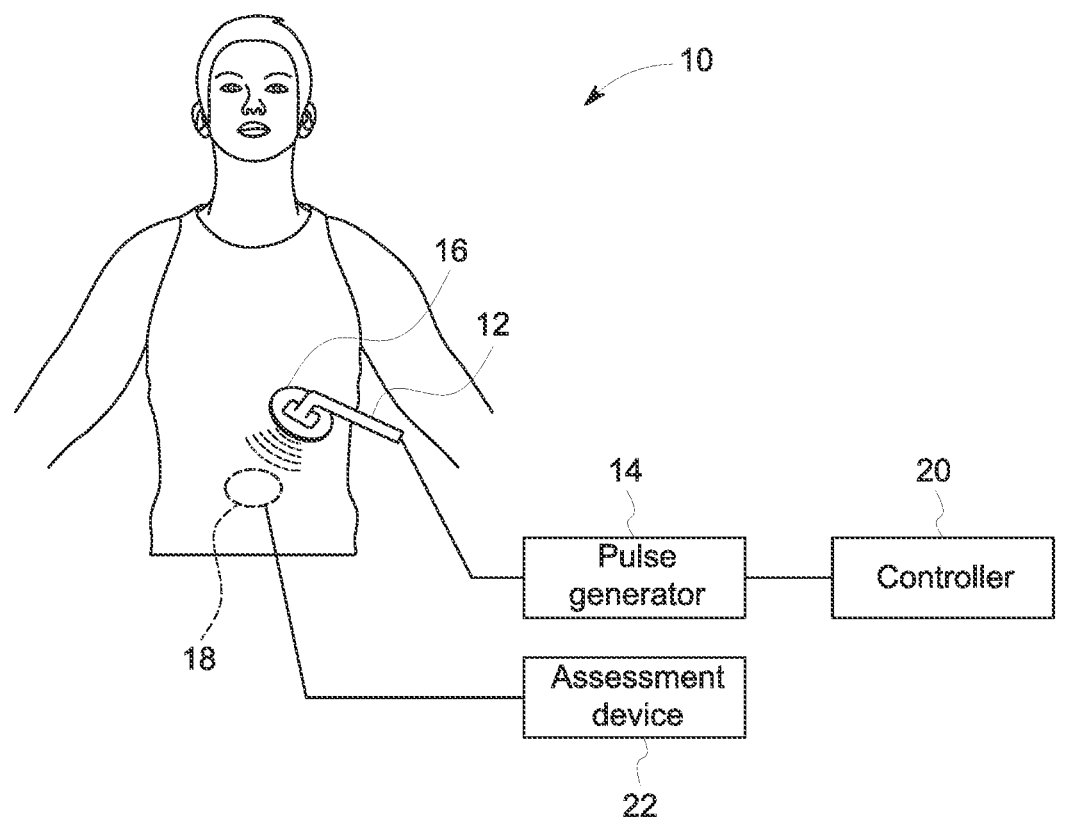
FIG. 1 is a schematic representation of a neuromodulation system using a pulse generator and a neuromodulation positioning patch according to embodiments of the disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example," "for instance," "such as," "e.g.," "including," "in certain embodiments", "in some embodiments", and "in one (an) embodiment."

Provided herein are techniques for noninvasive neuromodulation of targeted regions of interest as part of a treatment protocol that permits reproducible and reliable application of energy to a particular region or regions of interest over the course of the treatment protocol. The noninvasive neuromodulation may be applied via an energy application device (e.g., a therapy probe, an ultrasound therapy probe) that is positioned on a patient's skin and that delivers neuromodulating energy through the skin and to the region of interest. For certain patients, a treatment protocol may include energy application, e.g., noninvasive ultrasound or mechanical energy application, to a region of interest of the patient at intervals according to the patient's particular clinical needs and at doses associated with targeted physiological outcomes. Depending on the length of the interval (e.g., intervals of hours, days, or weeks) between energy applications, it may be inconvenient and cumbersome to have the patient receive neuromodulating energy in a doctor's office or hospital at each treatment time. Accordingly, it would be beneficial to permit the patient to receive the neuromodulating energy according to the treatment protocol at home or in a convenient outpatient setting, either via self-directed delivery or with the help of a family member or caregiver. However, because patients do not typically have skills or training in medical device operation, it may be challenging to train a patient to manage their own neuromodulation treatment. Further, each patient's treatment protocol may be personalized and vary from patient-to-patient according to variations in anatomy, clinical condition of the patient, and responsiveness of the patient to energy to generate the targeted physiological outcome. For example, a treatment protocol for treating a particular disorder may target a particular region of interest (e.g., a region of a liver, pancreas, or other tissue). An effective energy application site associated with neuromodulating energy targeting the region of interest may be at one site for one patient and a slightly different site for another patient due to differences in patient anatomy. Such sites may also include areas on the patient's back or side that are difficult to reach while holding a therapy probe, and even if reached, difficult for the patient to target in an accurate manner for repeated doses. Further, identification of the desired region of interest and the associated treatment position on the skin to achieve energy delivery to the region of interest may involve complex imaging devices that are not widely available and that add time to each dose of a multi-dose treatment protocol.

The neuromodulation techniques disclosed herein facilitate identification of a treatment position on the patient's skin for an energy application device and positioning of a neuromodulation positioning patch at or around the treatment position. For example, if a patient is prescribed a multi-dose treatment protocol that occurs over several days or weeks, the neuromodulation positioning patch may be applied to the patient at the beginning of the treatment protocol and may remain in place until the treatment protocol is complete to facilitate correct positioning of an energy application device. The neuromodulation positioning patch includes a support structure that reversibly fits or mates with an energy application device (e.g., a therapy probe) and positions the energy application device at the treatment position for accurate targeting of the region of interest via application of neuromodulating energy. The treatment position is a location on the patient's body that, when the energy application device is positioned at the treatment position as provided herein, the energy applied at (and through) the treatment site affects a desired region of interest in the patient's body to achieve a targeted physiological outcome. Such techniques may guide patients and/or their caregivers to administer their own treatments accurately.

In one embodiment, the neuromodulation positioning patch may at least partially support and orient the therapy probe so that the patient or caregiver need not apply pressure or, in certain embodiments, hold the therapy probe to maintain the therapy probe in the correct position. This may reduce the variability in dose application that may be the result of different caregivers orienting and/or positioning the therapy probe at slightly different positions misaligned or partially aligned with the treatment position. Further, differences in pressure of the probe to the skin at the treatment position may also result in undesired applied dose variability. An additional benefit of the disclosed techniques is that the neuromodulation positioning patch permits one-time identification of the region of interest and treatment position on the patient's skin. Once identified, the neuromodulation positioning patch is positioned in place. At subsequent dose applications, the complex imaging associated with identification of the region of interest need not be performed. Accordingly, the dose application is faster and may take place at home or in outpatient settings without complex imaging devices, resulting in greater flexibility for receiving neuromodulating energy according to a treatment protocol. The neuromodulation positioning patch may be multifunctional and configured to couple to a therapy probe as well as to an imaging probe via an adapter structure.

To that end, the disclosed neuromodulation techniques may be used in conjunction with a neuromodulation system configured to be used to administer neuromodulating energy as part of a treatment protocol. FIG. 1 is a schematic representation of a system 10 using a neuromodulation positioning patch supporting an energy application device to achieve neuromodulating effects such as neurotransmitter release and/or activation of components (e.g., the presynaptic cell, the postsynaptic cell) of a synapse in response to an application of energy. The depicted system includes a pulse generator 14 coupled to an energy application device 12 (e.g., an ultrasound therapy probe). The energy application device is coupled to a neuromodulation positioning patch 16 that is in position on a subject's skin and that holds or supports the energy application device 12 at a treatment position during application of the neuromodulating energy. The energy application device 12 is configured to receive energy pulses, e.g., via leads or wireless connection, that in use are directed to a region of interest 18 of an internal tissue or an organ of a subject (e.g., a peripheral tissue), which in turn results in a targeted physiological outcome. In the depicted embodiment, the neuromodulation positioning patch 16 is positioned on a hard-to-reach location on a subject's back. However, it should be understood that the neuromodulation positioning patch 16 may be applied to align with suitable treatment sites depending on the clinical needs of the subject.

In certain embodiments, the energy application device 12 and/or the pulse generator 14 may communicate wirelessly, for example with a controller 20 that may in turn provide instructions to the pulse generator 14. In other embodiments, the pulse generator 14 may be integrated within the controller 20. The energy application device 12 may be operated by a caregiver and positioned via the neuromodulation positioning patch 16 on or above a subject's skin such that the energy pulses are delivered transdermally to a desired internal tissue (e., a peripheral tissue that includes one or more peripheral axon terminals). Once positioned to apply energy pulses to the desired treatment position via coupling to the neuromodulation positioning patch 16, the system 10 may initiate neuromodulation of one or more nerve pathways to achieve targeted physiological outcome or clinical effects.

In certain embodiments, the system 10 may include an assessment device 22 that is coupled to the controller 20 and that assesses characteristics that are indicative of whether the targeted physiological outcome of the modulation have been achieved. In one embodiment, the targeted physiological outcome may be local. For example, the modulation of one or more nerve pathways may result in local tissue or function changes, such as tissue structure changes, local change of concentration of certain molecules, tissue displacement, increased fluid movement, etc., as disclosed herein. The targeted physiological outcome may be a goal of the treatment protocol. By way of example, the targeted physiological outcome may include hormone secretion (such as secretion of insulin from the pancreas or ghrelin from the GI), cell viability, and/or cell or hormonal stability.

The neuromodulation positioning patch 16 may be used in conjunction with a neuromodulation treatment protocol as provided herein. Neuromodulation of one or more nerve pathways to achieve a targeted physiological outcome may result in systemic or non-local changes, and the targeted physiological outcome may be related to a change in concentration of circulating molecules or a change in a characteristic of a tissue that does not include the region of interest to which energy was directly applied. In one example, the displacement may be a proxy measurement for a desired modulation, and displacement measurements below an expected displacement value may result in modification of modulation parameters until an expected displacement value is induced. Accordingly, the assessment device 22 may be configured to assess concentration changes in some embodiments. In some embodiments, the assessment device 22 may be an imaging device configured to assess changes in organ size position, and/or tissue characteristics. In some embodiments, the assessment device 22 monitors changes in blood pressure, indicative of arterial resistivity changes associated with treatment. In another embodiment, the assessment device 22 may be a circulating glucose monitor. While the depicted elements of the system 10 are shown separately, it should be understood that some or all of the elements may be combined with one another. In another embodiment, the assessment device may assess local temperature rises of the tissue, which may be detected using a separate temperature sensor or ultrasound imaging data from the energy application device 12 when configured for ultrasound energy application. Assessment of speed of sound differences may be detected through difference imaging techniques pre/during/post therapy.

Based on the assessment, the modulation parameters of the controller 20 may be altered such that an effective amount of energy is applied. For example, if a desired modulation is associated with a change in concentration (circulating concentration or tissue concentration of one or more molecules) within a defined time window (e.g., 5 minutes, 30 minutes after a procedure of energy application starts) or relative to a baseline at the start of a procedure, a change of the modulation parameters such as pulse frequency or other parameters may be desired, which in turn may be provided to the controller 20, either by an operator or via an automatic feedback loop, for defining or adjusting the energy application parameters or modulation parameters of the pulse generator 14 until the modulation parameters result in an effective amount of energy being applied.

The system 10 as provided herein may provide energy pulses according to various modulation parameters as part of a treatment protocol to apply the effective amount of energy. For example, the modulation parameters may include various stimulation time patterns, ranging from continuous to intermittent. With intermittent stimulation, energy is delivered for a period of time at a certain frequency during a signal-on time. The signal-on time is followed by a period of time with no energy delivery, referred to as signal-off time. The modulation parameters may also include frequency and duration of a stimulation application. The application frequency may be continuous or delivered at various time periods, for example, within a day or week. Further, the treatment protocol may specify a time of day to apply energy or a time relative to eating or other activity. The treatment duration to cause the targeted physiological outcomes may last for various time periods, including, but not limited to, from a few minutes to several hours. In certain embodiments, treatment duration with a specified stimulation pattern may last for one hour, repeated at, e.g., 72 hour intervals. In certain embodiments, energy may be delivered at a higher frequency, say every three hours, for shorter durations, for example, 30 minutes. The application of energy, in accordance with modulation parameters, such as the treatment duration, frequency, and amplitude, may be adjustably controlled to achieve a desired result.

The energy application device 12 may be configured as an extracorporeal noninvasive device. The energy application device 12 may be an extracorporeal noninvasive ultrasound therapy probe including an ultrasound transducer or mechanical actuator. For example, the energy application device 12 may be configured as a handheld ultrasound probe. Further, in addition to handheld configurations, the energy application device 12 may include steering mechanisms responsive to instructions from the controller 20. The steering mechanisms may orient or direct the energy application device 12 towards the region of interest 18, and the controller 20 may then focus the energy application onto the region of interest 18.

In operation, the neuromodulation positioning patch 16 may be configured to hold or support the energy application device 12 during dose delivery. In addition, the neuromodulation positioning patch 16 is configured to hold or support an imaging probe to acquire images to identify or verify a desired treatment site. As provided herein, the imaging probe may be part of the system 10 and may also operate using the same or similar components that control application of energy via the energy application device 12. That is, the imaging probe may use a pulse generator 14 under control of a controller 20. In one embodiment, the ultrasound therapy transducer and/or the imaging transducer as disclosed herein include a MEMS transducer, such as a capacitive micromachined ultrasound transducer. In one embodiment, a therapy transducer and an imaging transducer may be integrated within a unitary energy application device 12. However, in other embodiments, the energy application device 12 and the imaging probe are separate devices.

Figure 2:
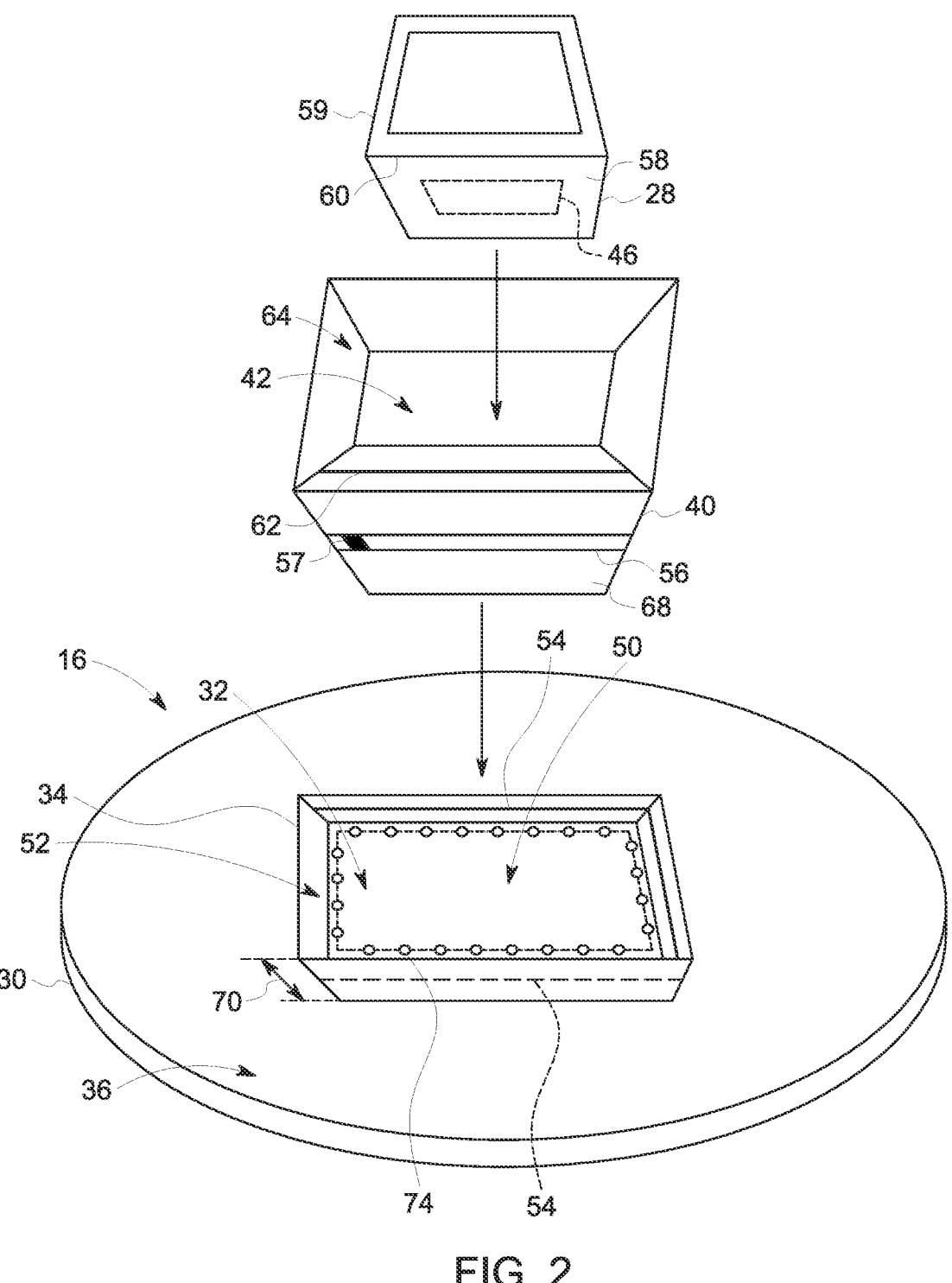
FIG. 2 is a schematic representation of a neuromodulation positioning patch and a dock and ultrasound imaging probe in an uncoupled configuration according to embodiments of the disclosure.

Because the energy application device 12 and an imaging probe may have different configurations, the neuromodulation positioning patch 16 includes features that adapt the neuromodulation positioning patch 16 to couple to both types of devices. FIG. 2 is a schematic illustration of the neuromodulation positioning patch 16 applied to a subject and configured to receive an imaging probe 28. The neuromodulation positioning patch 16 includes a conformable substrate 30 forming an aperture or opening 32 through the conformable substrate to permit viewing of the patient's skin through the opening 32 when the neuromodulation positioning patch 16 is applied (e.g., adhered) in place. The conformable substrate 30 may be formed from a fabric, paper, or conformable polymer. The opening 32 is surrounded by a resilient frame 34 that protrudes from a top surface 36 of the conformable substrate 30. The top surface 36 opposes a surface of the conformable substrate 32 that is applied to the patient's skin.

In certain implementations, the neuromodulation positioning patch 16 is intended for wear over several days. Accordingly, the conformable substrate 32 may be more comfortable for the subject than a rigid substrate. However, in certain embodiments, portions of the conformable substrate 32 may be replaced or reinforced with rigid elements to facilitate support of larger or heavier coupled probes.

In operation in the imaging configuration, the resilient frame 34 is configured to couple to a removable dock 40. The removable dock 40 forms a passage that terminates in a distal opening 42 that accommodates the imaging probe 28. The resilient frame 34 couples to the removable dock 40 such that the distal opening 42 of the dock 40 is positioned within the opening 32. In this manner, an imaging transducer 46 of the imaging probe 28 is correctly positioned at the treatment site 50 when coupled to the dock 40. In one embodiment, the dock 40 is configured to directly contact the patient's skin at the distal opening when coupled to the resilient frame 34. The resilient frame 34, the dock 40, and/or the imaging transducer 46 of the imaging probe 28 may include one or more mating features that facilitate their respective coupling. For example, an interior wall 52 of the resilient frame 34 may include one or more grooves or protrusions 54 configured to mate to complementary features 56 on an exterior wall 68 of the dock 40. Similarly, an exterior wall 58 of a housing 59 of the imaging probe may also include one or more mating features 60 configured to mate to complementary features 62 on an interior wall 64 of the dock 40. The resilient frame 34, the dock 40, and/or the imaging transducer 28 maybe formed from rigid or semi-rigid materials, such as polymers having a hardness of 10-50 Shore D.

As disclosed herein, the mating features (e.g., mating features 54, 56, 60, 62) may be configured as grooves, recesses, protrusions, locking features, threaded features, snaps, etc. Further, certain components may additionally or alternatively be configured for interference fits. The mating features may also include one or more signal generators or indicators (e.g., RFID chip 57) that, when mated to their complementary feature, generate or provide a signal to indicate successful mating. The mating features may be configured to permit only one orientation of mating components relative to one another. For example, the resilient frame 34 and the dock 40 may only mate with one another in one orientation. Further, the dock 40 may also accommodate the imaging probe 28 in only one orientation. Such an arrangement may facilitate correct orientation of the imaging probe 28 within the neuromodulation positioning patch 16 and relative to the treatment site 50.

In the depicted configuration, the resilient frame 34 protrudes from the top surface 36 by a distance 70 (e.g., less than 3 cm, less than 1 cm). The protrusion is in a direction away from the subject. In certain embodiments it is desirable for the resilient frame 34 to be relatively low profile to cause less discomfort for the subject over time. Further, by configuring the dock 40, which may have a relatively larger profile, to be removable, the neuromodulation positioning patch 16 may be configured only temporarily in the higher profile (greater protrusion from the skin) imaging configuration. In other embodiments, the resilient frame 34 may be configured to have telescoping or adjustable height walls 52 so that the resilient frame 34 may switch between an undocked or empty configuration that has a lower profile relative to a docked or operational configuration.

The initial positioning of the neuromodulation positioning patch 16 on the patient may be performed by an imaging technician or physician. The operator acquires images until an image that includes the region of interest 18 is acquired. The position of the imaging probe 28 on the skin at the time of acquisition of images of the region of interest 18 may correspond to the treatment position 50. In one embodiment, an indicator 74 such as a mark, temporary tattoo, or a sticker may be applied to the skin to the treatment position 50 to guide correct positioning of the opening 32 to be aligned with, i.e., positioned on or over the treatment position 50. Further, the indicator 74 may be shaped to align with the opening 32 to assist correct positioning of the neuromodulation positioning patch 16. In one embodiment, the neuromodulation positioning patch 16 may be configured to apply and/or refresh the indicator 74. For example, the conformable substrate 30, the resilient frame 34, and/or the removable dock 40 may include ink or other transferable materials configured to mark the subject at the time of application of the neuromodulation positioning patch 16. Because the neuromodulation positioning patch 16 may be moved along the subject to try a few positions before being eventually adhered in place, the transferable materials may be actuated or triggered via user action. For example, the transferable materials may be pressure sensitive, and may be applied when sufficient pressure is applied. In another embodiment, successful mating of the removable dock 40 and the resilient frame 34 opens a reservoir within the removable dock 40 and the resilient frame 34 that contains the transferable material and that opens to a patient contact side of the neuromodulation positioning patch 16. In another embodiment, user depression of a button or actuator releases the transferable material. In this manner, the desired position of the neuromodulation positioning patch 16 may be marked such that a new neuromodulation positioning patch 16 can be applied to the subject when the prior device is due for replacement.

The indicator 74 be applied to mark the preferred position of the neuromodulation positioning patch 16 after identification of the desired treatment site 50. Such identification may constitute a first pass positioning that permits the subject or the operator to adhere the neuromodulation positioning patch 16 in the correct position based on the imaging data. However, additional imaging data may be desired to verify the treatment position 50 and/or to acquire information for fine steering of the therapy probe. That is, an imaging probe 28 supported at the treatment site 50 by the neuromodulation positioning patch 16 may additionally or alternatively acquire imaging data to verify the treatment site 50 and/or to provide to the therapy probe for steering of the ultrasound therapy beam by the controller 20. It should be understood that the treatment position 50 as provided herein may include an angle, orientation, and/or pose of the energy application device 12. The position information may also include an assessment of contact or pressure on the subject.

In certain embodiments, the ultrasound imaging probe 28 may be any suitable probe that is capable of acquiring image data of the internal tissue near and around the target tissue containing the region of interest 18. If the first pass image acquisition used to initially position the neuromodulation positioning patch 16 is successful, lower complexity ultrasound imaging probes 28 may be used for acquisition of the additional verification or beam-steering image data. For example, the images from a high resolution first pass may be accessed and used to supplement additional lower quality image data. Accordingly, the caregiver may have flexibility in the image resolution capability when selecting an available ultrasound image probe 28 to acquire the additional image data. Thus, more commonly available lower complexity ultrasound image probes 28 may be suitable.

Figure 3:
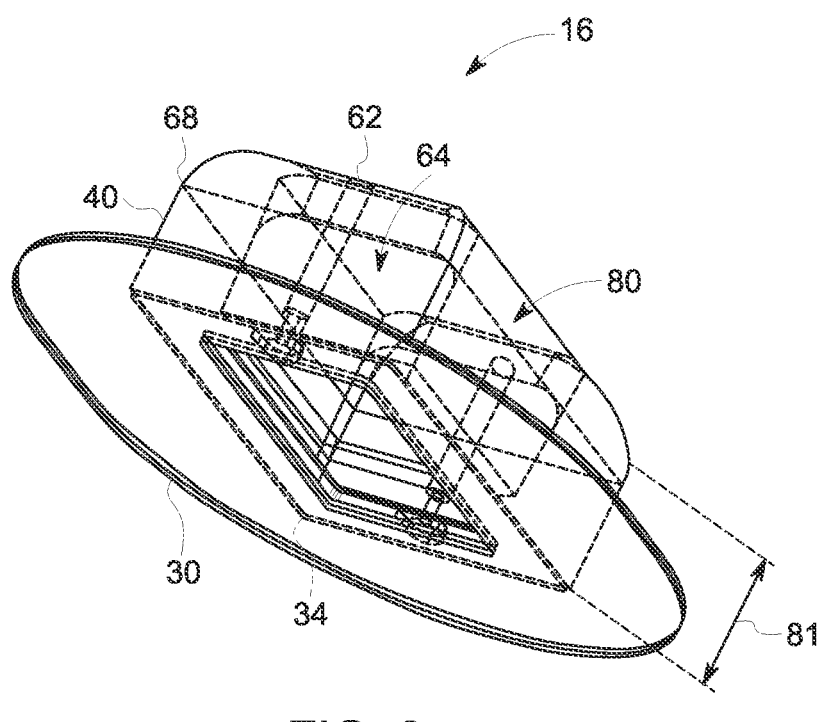
FIG. 3 is a schematic representation of a neuromodulation positioning patch and a dock according to embodiments of the disclosure.
Figure 4:
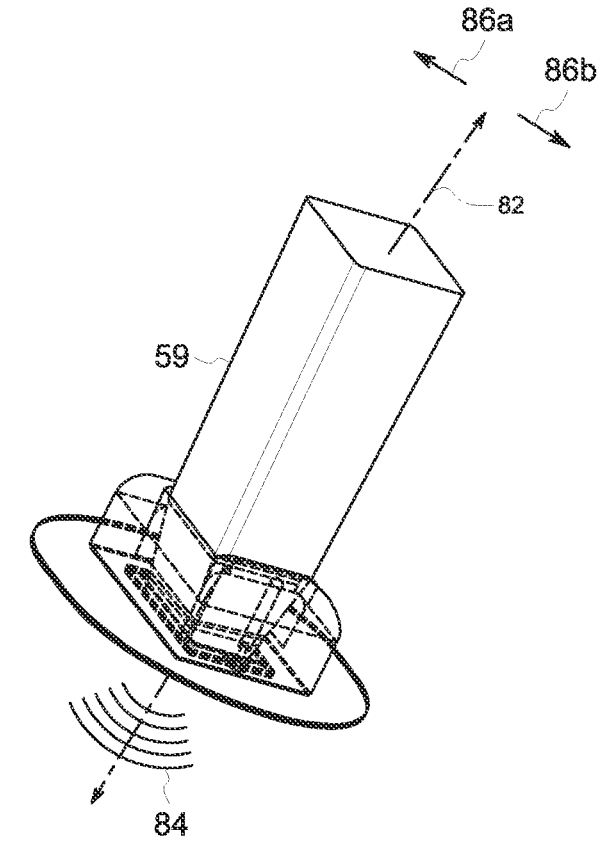
FIG. 4 is a schematic representation of a neuromodulation positioning patch and a dock coupled to a probe according to embodiments of the disclosure.

FIG. 3 shows a neuromodulation positioning patch 16 with a mated removable dock 40 that is ready to receive a probe, such as the imaging probe 28, as shown in the mated configuration of FIG. 4. The probe is inserted via a proximal opening 80 of the removable dock 28. While the depicted embodiment in FIG. 4 illustrates a mated imaging probe 28, it should be understood that the removable dock 40 may, in an embodiment, also be configured to receive a therapy probe. Further, in embodiments in which the imaging probe 28 and the therapy probe are implemented as a unitary device, the removable dock 40 or a different removable dock 40 may receive the unitary device.

The removable dock 40 provides a resilient support to the mated probe (e.g., the imaging probe 28) to maintain a desired orientation of the probe relative to the subject. The interior walls 64 directly contact and support the probe housing 59 to maintain the orientation along a desired axis, e.g., an axis 82 through the housing 59 and aligned with a direction of the applied energy 84. The probe may be maintained to avoid tilting (e.g., along arrows 86) such that the applied energy is generally along a stable axis during activation of the probe. In addition, the mating features 62 of the dock may also serve to facilitate positioning of the probe. The exterior walls 68 of the dock 40 are defined by a height 81 that increases the profile of the neuromodulation positioning patch 16 beyond the distance 70 by which the frame 34 extends from the conformable substrate. In one embodiment, the dock 40 has a distal recess or groove that mates with the resilient frame 34. In such an embodiment, the mated dock 40 overlaps with the resilient frame 34. The distance 81 is greater than the distance 70 by which the frame 34 extends from the conformable substrate 30. In an embodiment, the height 81 of the dock 40 is at least 2, 2.5, or 3 times the distance 70. As discussed herein, the increase in the profile of the neuromodulation positioning patch 16 with the mated dock 40 is temporary.

The positioning and adhering of the patch 16 on the patient sets the x-y position as well as the spin of the probe (e.g., the energy application device 12 and/or the imaging probe 28). In another embodiment, the dock 40 or frame 34 may permit fine adjustment of the tilt, rock, and/or compression of probe (pressure on the skin). For example, the dock 40 or frame 34 may include compressible foam or putty disposed on the interior walls 64 that permits angling of the probe (e.g., along arrows 86) until a desired orientation is achieved. The desired orientation may be associated with improved acquired image data and/or improved contact with or pressure applied to the subject's skin. The putty or foam holds the probe at the desired orientation. In other embodiments, the dock 40 or the frame 34 may include other features that permit adjustment of the probe orientation, such as compressible or memory metal walls. In another example, the orientation may be tuned via locking adjustable mechanical linkages in each adjustable dimension—specifically tilt, rock, and compression. For compression, setting the Z position of the probe (e.g., along the axis 82) may be adjusted such that when the probe is locked into the dock, the probe face may push past the frame 34 of the wearable patch 16 into the skin to ensure good contact or to achieve a specific target contact force. The positioning of the probe relative to the frame 34 may permit several different position slots along the axis 82. In one example, the frame 34 and/or dock 40 may include two or more internal mating features 54, 56, e.g., grooves, at different positions along the Z axis. The grooves may be configured to be at least partially conformable (formed with flexible edges) such that the user may push through successive mating features 54, 56 with moderate force until a desired position of the probe along the axis 82 is achieved. In another example, the probe, the frame 34, and/or the dock 40 may include deployable locking features. For example, the probe may be adjusted within the dock 40 or the frame 34 (in embodiments without the dock 40) until a desired position is reached. The user may then depress a button on the dock 40 or the frame 34 that causes actuation of a locking feature towards the probe that contacts the probe housing or a mating featuring on the probe to lock the probe in position.

Figure 5:
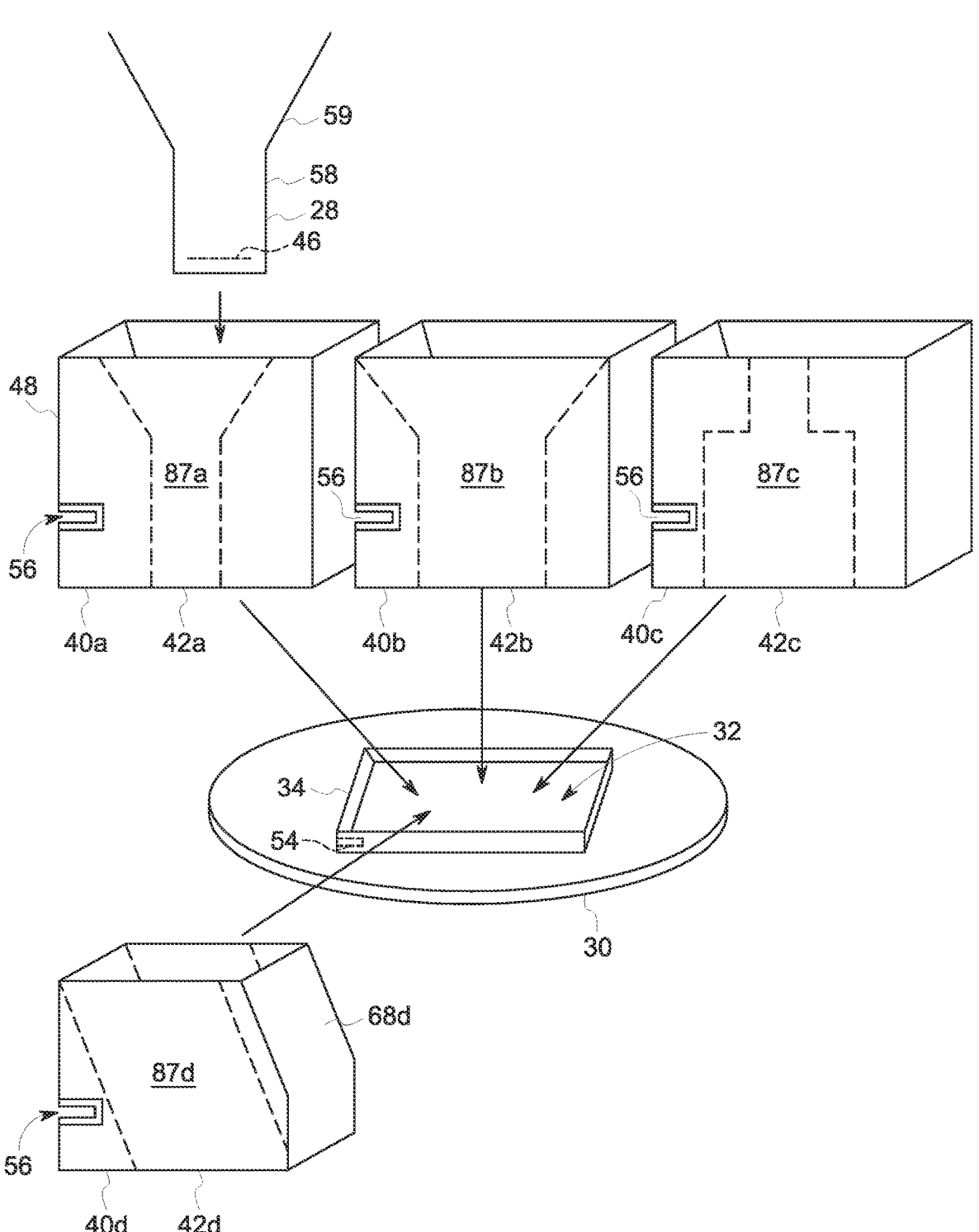
FIG. 5 is a schematic representation of a neuromodulation positioning patch kit including different docks for various configurations of according to embodiments of the disclosure.

FIG. 5 is a schematic representation of a neuromodulation positioning patch kit including different docks 40 that mate with different shapes of an ultrasound imaging probe 28 to facilitate use of a variety of types and/or configurations. In one embodiment, the neuromodulation positioning patch 16 may be provided as a kit with different types of docks 40 that may be selected based on an available imaging modality. A caregiver may wish to use an available or familiar imaging device to acquire image data that permits the initial positioning of the neuromodulation positioning patch 16 and/or verification of the position after positioning. By providing swappable docks 40 that include different shaped passages 87, various available imaging probes may be used. In the depicted embodiments, different docks 40a, 40b, 40c, 40d may be shaped such that their exterior walls 68 are generally the same to permit each of the different docks 40a, 40b, 40c to mate with the resilient frame 34. In an embodiment, the nonmating portions of the exterior walls 68 may vary in size and shape between the different docks 40. Further, each of the different docks 40a, 40b, 40c, 40d may include identical mating features on their exterior walls 68. In an alternative embodiment, each of the different docks 40a, 40b, 40c, 40d may include unique mating features 56 that, when mated with the resilient frame, trigger activation of an identification signal of a particular type of dock 40 that in turn may be provided by the ultrasound imaging probe 28 to its controller (e.g., controller 20) as a verification procedure.

The internal shaped passages 87a,87b,87c, 87d are configured such that only certain or a particular type of ultrasound imaging probe 28 will fit within each individual dock 40 and, in one embodiment, will fit only in a particular orientation. The internal shaped passages 87 may include grooves, notches, or other shaped features that are associated with a particular type of ultrasound imaging probe 28. In one embodiment, the kit may also include a universal dock 40 with a larger or generally annular passage 87 that permits insertion of multiple types of ultrasound imaging probes 28. The shaped passages terminate in respective distal openings 42 that position the transducer 46 in the desired treatment (or imaging) position. An individual dock 40 may also be sized and shaped to permit the operator to try different probe angles or orientations. For example, certain internal passages 87 may be oriented at different angles relative to one another (e.g., internal passage 87a vs. internal passage 87d) such that the retained probes are correspondingly held at different angles. In addition, the kit may include one or more adjustable docks 40 that permit movement of the probe within the internal passage 87 until a desired position is reached. For example, the dock 40 with an oversized or universal-sized internal passage 87 may be provided with shims, foam, gel, locking mechanical linkages, or other temporary stabilizing material that can be inserted into the internal passage 87 to fill any gaps between the internal walls 64 and the housing 59 of the probe and to maintain the probe in the desired orientation.

The kit may also include multiple neuromodulation positioning patches 16, for example having different sizes and shapes for application to different treatment sites. Further, it should be understood that certain components of the kit may be disposable (the neuromodulation positioning patch 16) while other components may be reusable (the docks 40).

Figure 6:
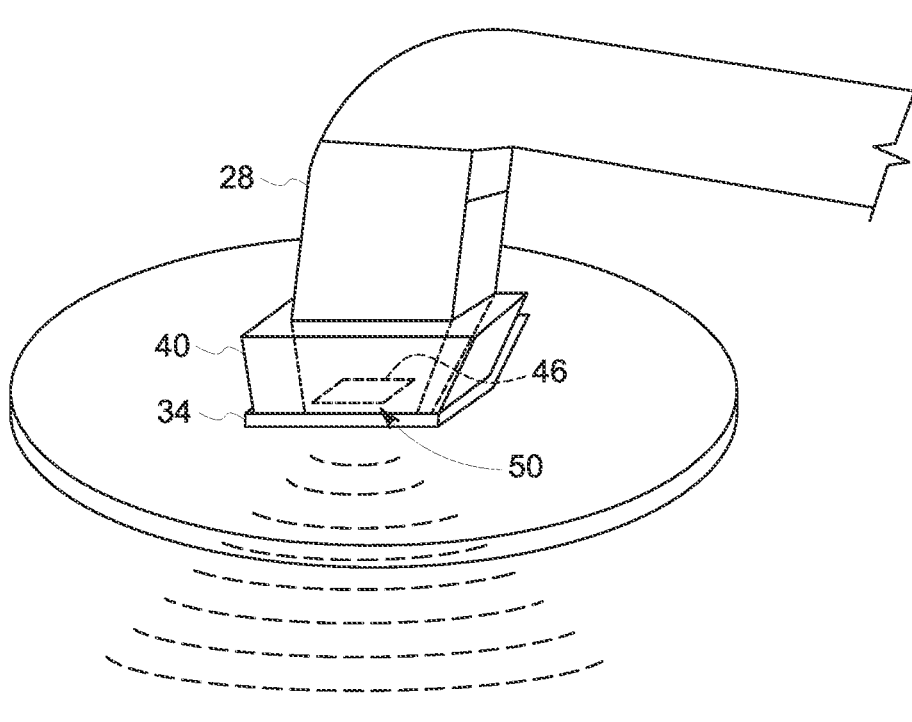
FIG. 6 is a schematic representation of a neuromodulation positioning patch coupled to a ultrasound imaging probe via a dock according to embodiments of the disclosure.

FIG. 6 is a schematic representation of a neuromodulation positioning patch 16 coupled to the ultrasound imaging probe 28 via the dock 40 in the coupled or imaging configuration. In the coupled configuration, the imaging transducer 46 of the ultrasound imaging probe 28 is aligned with the treatment position 50 on the patient's skin and imaging energy may be applied. As shown, the dock 40, when mated with the resilient frame 34, may also provide support to the ultrasound imaging probe 28 to hold the ultrasound imaging probe 28 with the desired pressure and at the desired position and orientation relative to the treatment site 50 during the course of the acquisition of image data. After completion of the acquisition of image data, the dock 40 and the ultrasound imaging probe 28 may be removed from the neuromodulation positioning patch 16 so that the subject may continuously wear only the less complex and expensive components of the system 10 that may be readily replaced if damaged.

Figure 7:
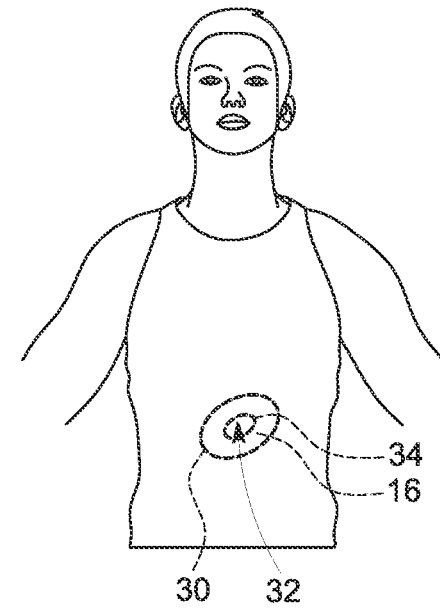
FIG. 7 is a schematic representation of an empty or uncoupled neuromodulation positioning patch worn by a subject.

FIG. 7 is a schematic representation of an empty or uncoupled neuromodulation positioning patch 16 worn by a subject. In the uncoupled configuration, the neuromodulation positioning patch 16 may include only the conformable substrate 30 and the resilient frame 34. As discussed herein, the conformable substrate 30 may be reinforced by one or more rigid or semi-rigid layers or structures to maintain the integrity of the position of the neuromodulation positioning patch 16 on the subject's skin and to support any mated structures. The resilient frame 34 may be relatively low profile for comfort and may be rounded or may include cushioning layers or bumpers to prevent discomfort when pressed. As noted, in the uncoupled configuration, the neuromodulation positioning patch 16 is ready to receive either the ultrasound imaging probe 28 or an energy application device, depending on the next step in the treatment protocol. It should be understood that the patch 16 may be used in conjunction with various therapy protocols, such as those that occur over days, weeks, months, or even years. The patch 16 may be configured to be replaced as needed, and a new patch 16 may be applied to the subject according to the techniques provided herein. Further, additional image acquisition over the course of the treatment may be used to spot-check the initial placement of the patch 16. Still further, additional images may be acquired such that the patch placement may be responsive to changes in the subject's physiology over time. For example, ultrasound treatment for metabolic disorders according to the techniques herein may lead to weight loss, which may influence correct patch positioning by changing the depth of the region of interest relative to the skin.

While the conformable substrate 30 is depicted as having a generally annular configuration, it should be understood that other shapes are contemplated, including elongated shapes, rectangles, irregular shapes, etc. For example, a particular treatment site 50 may be associated with a particular shape of the conformable substrate 30 to achieve desired adhesion. Further, the opening 32 and the resilient frame 34 are depicted as being generally rectangular. However, the opening 32 and the resilient frame 34 may be configured as annular shapes elongated shapes, rectangles, irregular shapes, etc., depending on the size of the treatment site 50 and the size and shape of the energy application device 12 as well as the ultrasound imaging probe 28.

Further, a perimeter of the opening 32 may be completely bounded by the resilient frame 34 or may be mostly bounded (e.g., at least 75% bounded). The conformable substrate 30 and the resilient frame 34 may, in one embodiment, form a U-shape that permits a sliding motion to couple the energy application device 12 and/or the ultrasound imaging probe 28 to the neuromodulation positioning patch 16.

Figure 8:
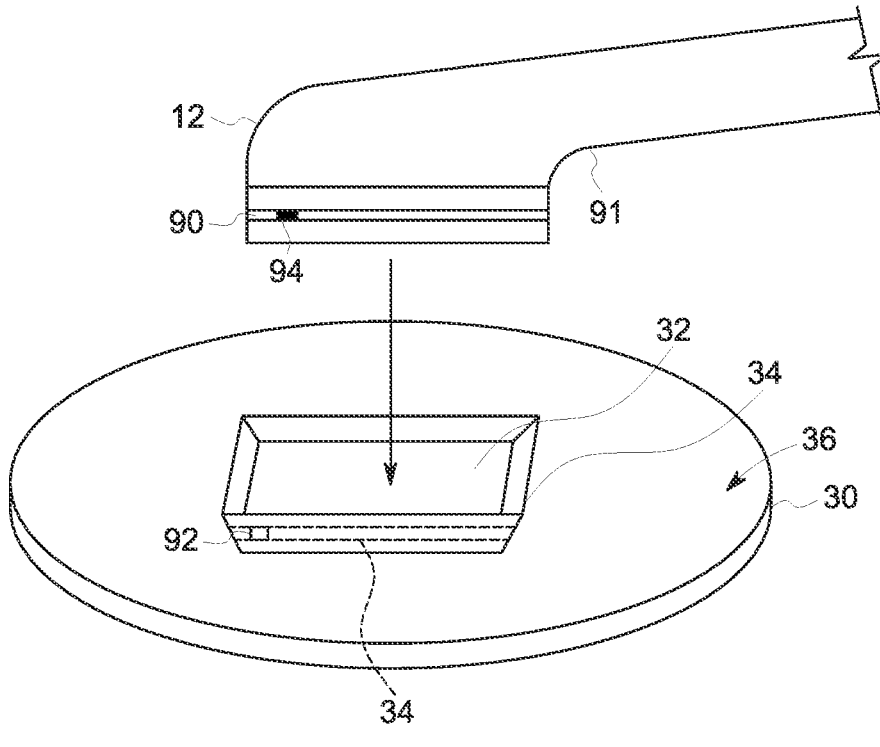
FIG. 8 is a schematic representation of a neuromodulation positioning patch and an ultrasound therapy probe configured to couple to a frame of the neuromodulation positioning patch in an uncoupled configuration according to embodiments of the disclosure.
Figure 9:
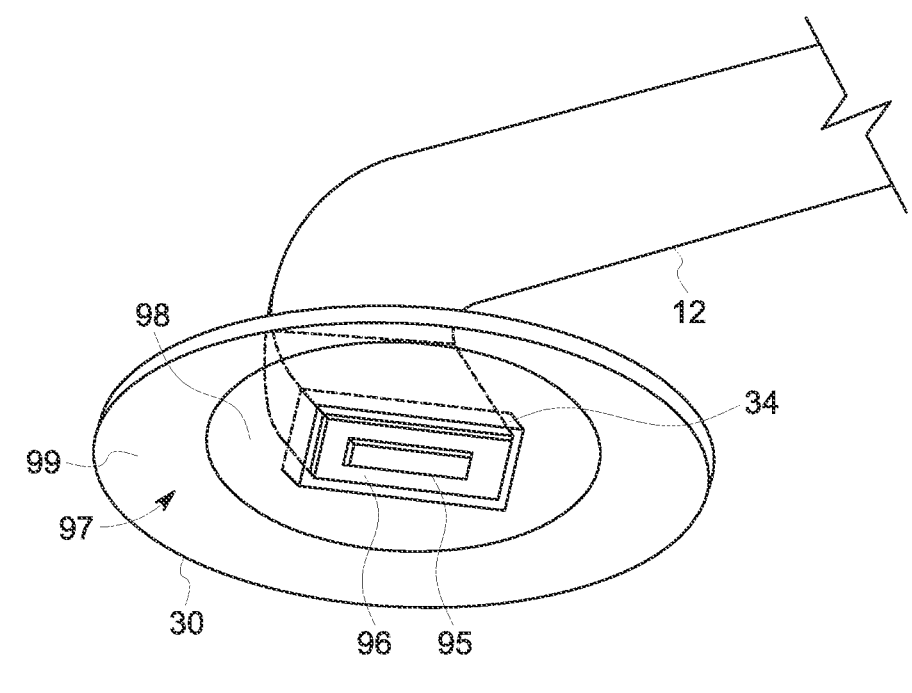
FIG. 9 is a bottom view of the neuromodulation positioning patch and coupled to the ultrasound therapy probe of FIG. 8.
Figure 10:
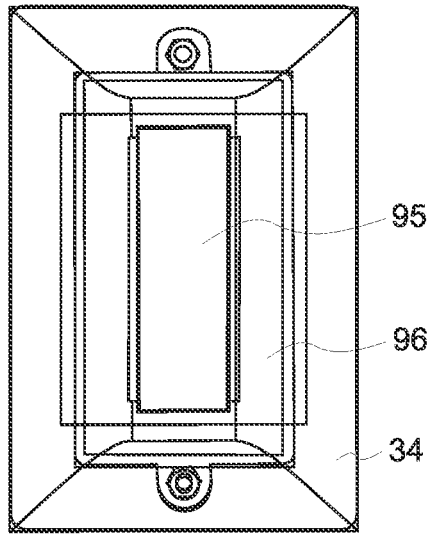
FIG. 10 is a bottom view of the frame of the neuromodulation positioning patch with the coupled to the ultrasound therapy probe of FIG. 8.

FIG. 8 is a schematic representation of a neuromodulation positioning patch and an energy application device 12 configured as an ultrasound therapy probe configured to couple to the resilient frame 34 of the neuromodulation positioning patch 16 in the uncoupled configuration. FIG. 9 is a bottom view of the neuromodulation positioning patch 16 coupled to the energy application device 12 (i.e., in the coupled configuration) of FIG. 8. FIG. 10 is a bottom view of the positioning of a transducer 95 of the energy application device 12 within the resilient frame 34 in which the energy application device 12 mates to fill the opening 32 formed by the frame 34. The coupling may be via the mating feature 54 of the resilient frame 34 that also couples to the dock 40 such that the mating feature 54 receives and couples to both the dock 40 and configured to couple to a complementary mating feature 90 formed in or disposed on a housing 91 of the energy application device 12. The coupling may also be via a separate dedicated mating feature, distinguishable (e.g., at a different position, differently sized or shaped) from a dock mating feature of the resilient frame 34 and configured to couple to the complementary mating feature 90. One or both of the mating features of the energy application device 12 and the resilient frame 34 may include signal elements, such as connector 92 and connector 94, that are activated by the coupling and that send a signal indicative of the successful coupling. For example, the connectors 92, 94 may be in direct contact when coupled to complete a circuit that, upon completion, is activated to send the signal. Upon coupling, the energy application device 12 may be at least partially supported by the resilient frame 34 and the conformable substrate 30 to remain in position within the opening 32 during energy application and to position the therapy transducer 95 such that a bottom surface 96 of the therapy transducer 95 is in contact with the patient's skin.

The application layer 97 of the neuromodulation positioning patch 16 includes an adhesive 99 that may at least partially cover the application layer 97 and that functions to adhere the neuromodulation positioning patch 16 to the patient's skin. In one embodiment, the adhesive is disposed on at least 50% of the surface area of the application layer 97. In one embodiment, the application layer 97 comprises a coupling gel region 98 comprising an ultrasound gel disposed on the application layer. The ultrasound gel may be pushed into the opening 32 upon application of the neuromodulation positioning patch 16. Accordingly, in certain embodiments, the energy application device 12 and/or the imaging probe 28 may directly contact the patient's skin. It should be understood that, as provided herein, the direct contact may include coupling of the skin to the probe head via a thin layer of ultrasound gel. The neuromodulation positioning patch 16 may also include a release layer (not shown) that, during storage, covers the application layer 97 to maintain the adhesive 99 and the coupling gel 98. The release layer, when present, is removed prior to application of the neuromodulation positioning patch 16.

Figure 11:
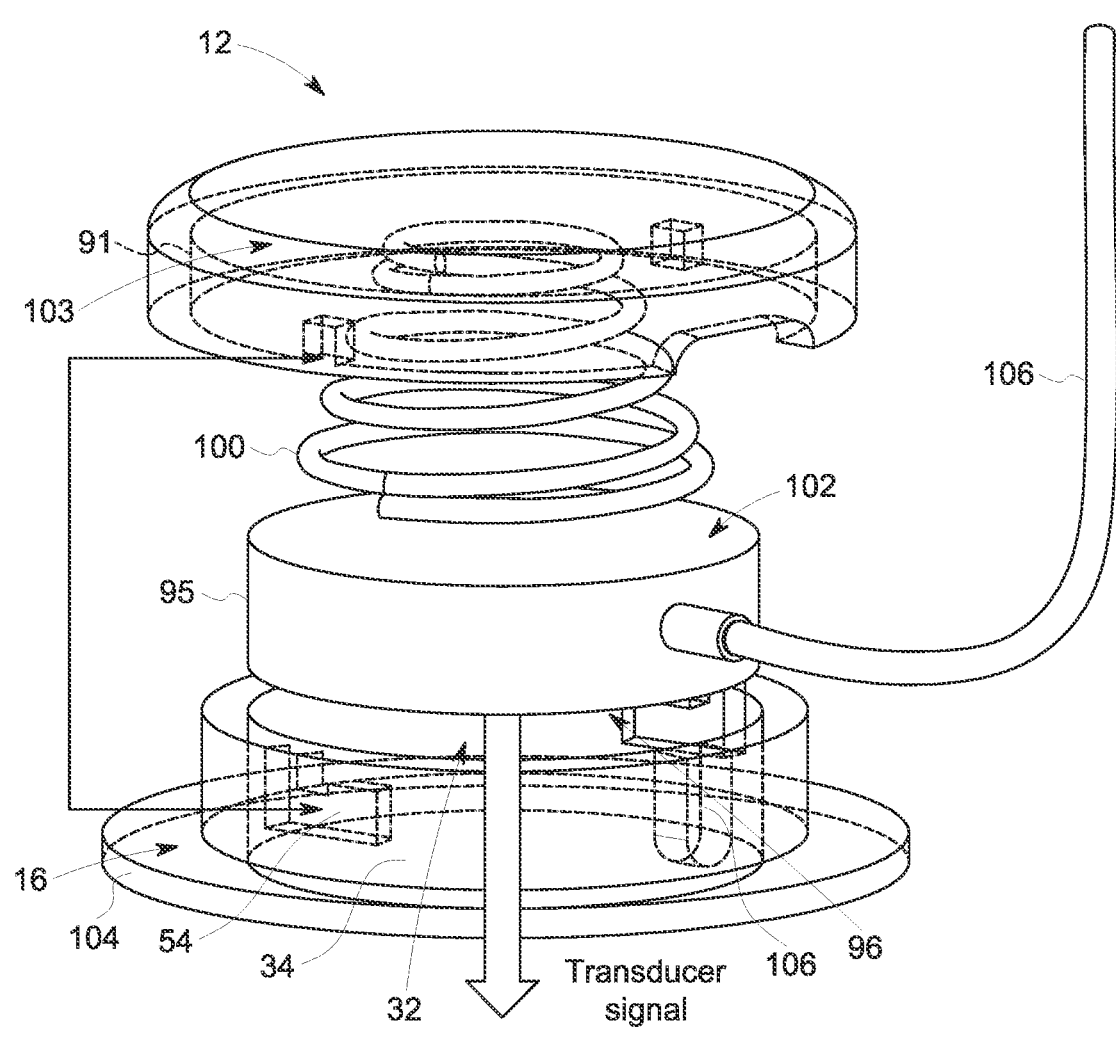
FIG. 11 is a component view of a neuromodulation positioning patch and an ultrasound therapy probe configured to couple to a frame of the neuromodulation positioning patch with a locking feature according to embodiments of the disclosure.

FIG. 11 is an exploded view of an embodiment of a neuromodulation positioning patch 16 configured to reversibly couple to an energy application device 12 that includes an ultrasound therapy transducer 95. The housing 91 of the energy application device 12 holds both the ultrasound therapy transducer 95 and a tension spring 100, with the tension spring 100 positioned between a top surface 102 of the ultrasound therapy transducer 95 and an interior surface 103 of the housing 91. In this manner, a bottom surface 96 of the therapy transducer 95 may be held with tension (e.g., light pressure) against the patient's skin when the energy application device is coupled to the frame 34 of the neuromodulation positioning patch 16.

The coupling may be between a mating feature 90 of the housing 91 of the energy application device 12, such as a protrusion, configured to lock with the complementary feature 54 of the frame 34, such as a shaped channel 104. In the depicted embodiment, the coupling may be a twist-to-lock arrangement to place the energy application device 12 within the opening 32 of the frame 34 and to position the protrusion within a locking region 105 extending away from a channel open of the shaped channel 104. However, other coupling arrangements (e.g., threaded coupling, snap fit, etc.) are also contemplated. The frame 34 may also include an opening configured to accommodate a cable 108 of the ultrasound therapy transducer 95. In this manner, the ultrasound therapy transducer 95 may be properly aligned with the frame 34 upon placement of the cable 108 within the opening 106 and coupling of the complementary mating features 54, 90.

Figure 12:
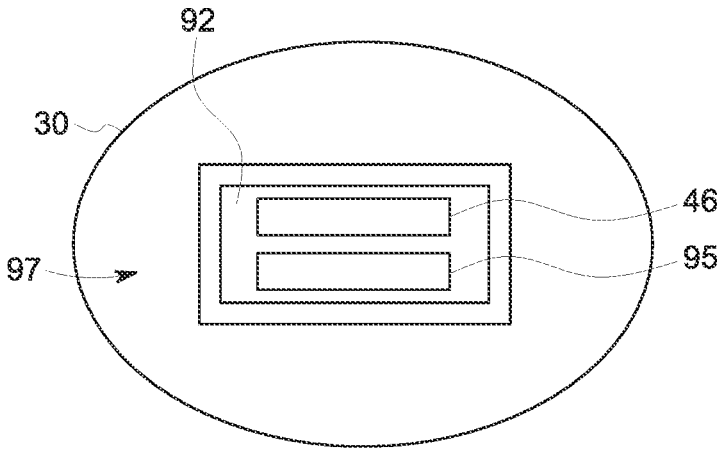
FIG. 12 is a bottom view of a neuromodulation positioning patch with an integral combination ultrasound therapy and imaging probe according to embodiments of the disclosure.

FIG. 12 is a bottom view of a neuromodulation positioning patch 16 showing the application layer 97 and with an integral combination ultrasound therapy transducer 95 and an imaging transducer 46 according to embodiments of the disclosure. While certain embodiments of the disclosure are discussed in the context of removable or swappable components of the neuromodulation positioning patch 16, the neuromodulation positioning patch 16 may also be implemented as an all-in-one device that is multifunctional. The imaging transducer 46 may be used for spatial selection of the region of interest 18 within the target tissue as well as verification of the position of the therapy transducer 95 that applies the neuromodulation energy.

Figure 13:
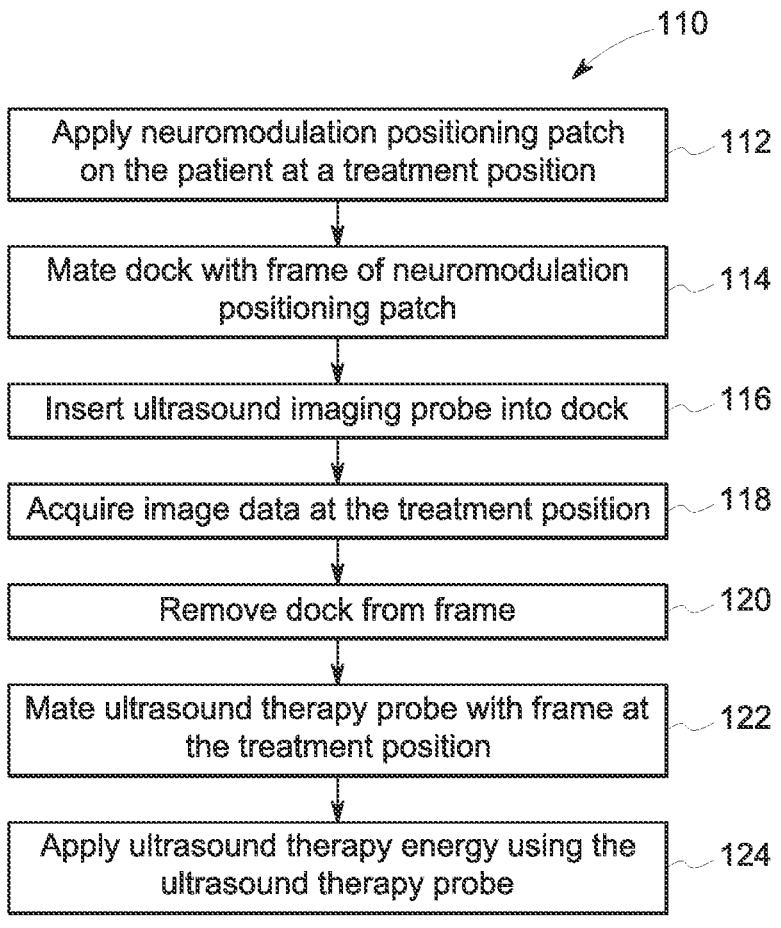
FIG. 13 is a flow diagram of a neuromodulation technique using a neuromodulation positioning patch according to embodiments of the disclosure.

FIG. 13 is a flow diagram of a neuromodulation method 110 using a neuromodulation positioning patch 16 according to embodiments of the disclosure. The method 100 may include steps of acquiring of image data that is used to identify a treatment site 50. In one embodiment, the image data is acquired in conjunction with the neuromodulation positioning patch 16. However, in other embodiments, the image data is previously acquired or acquired during a separate procedure. For example, the method 100 may include the step of applying the neuromodulation positioning patch 16 on the patient's skin at a treatment position 50 (block 112). As provided herein, the applying step may include pre-positioning steps in which the neuromodulation positioning patch 16 is in a temporary or nonadhered position. While the neuromodulation positioning patch 16 may be configured to be directly applied to the skin, it is also contemplated that there may be intervening structures (e.g., a thin fabric layer) between the neuromodulation positioning patch 16 and the skin in certain embodiments. As discussed herein, the initial positioning and application to the skin may be based on previously-acquired image data. In another embodiment, the neuromodulation positioning patch 16 may be temporarily positioned on the skin (i.e., without being adhered in position) until the correct treatment position 50 is identified via the acquired image data. Upon identification, the neuromodulation positioning patch 16 may then be adhered into position. During identification of the treatment position and/or during acquisition of additional image data that occurs over the total course of the treatment, the dock 40 may be coupled to or mated with the resilient frame 34 (block 114) and an ultrasound imaging probe 28 may be inserted into the dock (block 116) to acquire image data at the treatment position (block 118) or at a potential treatment position, whereby the acquired image data is assessed to determine if the potential treatment position is the treatment position 50. In one example, the neuromodulation positioning patch 16 is in a nonadhered configuration and the imaging probe 28 is docked within the neuromodulation positioning patch 16 and activated to acquire image data. The neuromodulation positioning patch 16 is adjusted to change position on the subject's skin, thus moving the docked imaging probe 28, until the treatment site 50 is confirmed. Once the neuromodulation positioning patch 16 is in position, release liners covering an adhesive 99 may be removed to secure the neuromodulation positioning patch 16 in position.

In another embodiment, the imaging probe 28 may be used without the neuromodulation positioning patch 16 for a first period of time to facilitate coarse position adjustment. Once the imaging probe is close to the treatment site 50, the imaging probe 28 may be coupled to the removable dock 48 and the neuromodulation positioning patch 16.

Subsequently, the imaging probe 28 and the dock 40 is removed from the resilient frame 34 (block 120), e.g., via uncoupling the complementary mating features or applying force to overcome an interference fit. The empty resilient frame 34 is then mated to the energy application device 12 (e.g., an ultrasound therapy probe) to position the therapy transducer at the treatment position 50 (block 122). Once mated, ultrasound therapy energy (neuromodulating energy) is applied (block 124).

Figure 14:
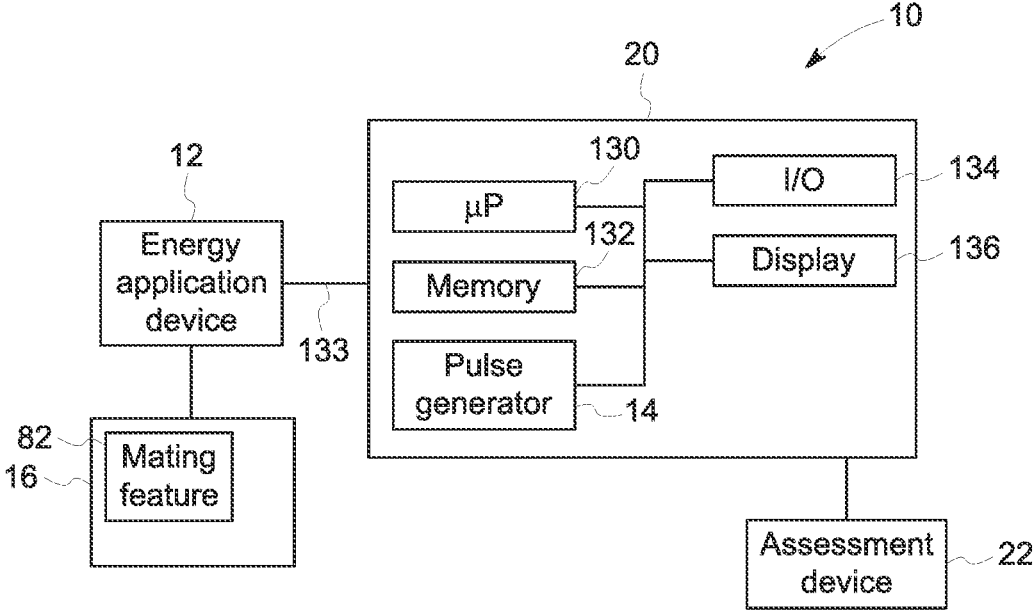
FIG. 14 is a block diagram of a neuromodulation system according to embodiments of the disclosure.

FIG. 14 is a block diagram of certain components of the system 10. As provided herein, the system 10 for neuromodulation may include a pulse generator 14 that is adapted to generate a plurality of energy pulses for application to a tissue of a subject. The pulse generator 14 may be separate or may be integrated into an external device, such as a controller 20. The controller 20 includes a processor 130 for controlling the device. Software code or instructions are stored in memory 132 of the controller 20 for execution by the processor 130 to control the various components of the device. The controller 20 and/or the pulse generator 14 may be connected to the energy application device 12 via one or more leads 133 or wirelessly. As disclosed herein, control of the energy application device 12 may further use inputs from one or more mating features 92 to detect successful mating of the energy application device 12 and the neuromodulation positioning patch 16.

The controller 20 also includes a user interface with input/output circuitry 134 and a display 136 that are adapted to allow a clinician to provide selection inputs or modulation parameters to modulation programs. Each modulation program may include one or more sets of modulation parameters including pulse amplitude, pulse width, pulse frequency, etc. The pulse generator 14 modifies its internal parameters in response to the control signals from controller device 20 to vary the stimulation characteristics of energy pulses transmitted through lead 133 to an subject to which the energy application device 12 is applied. Any suitable type of pulse generating circuitry may be employed, including but not limited to, constant current, constant voltage, multiple-independent current or voltage sources, etc. The energy applied is a function of the current amplitude and pulse width duration. The controller 20 permits adjustably controlling the energy by changing the modulation parameters and/or initiating energy application at certain times or cancelling/suppressing energy application at certain times. In one embodiment, the adjustable control of the energy application device to apply the effective amount of energy is based on information about a concentration of one or more molecules in the subject (e.g., a circulating molecule). If the information is from the assessment device 22, a feedback loop may drive the adjustable control. For example, a diagnosis may be made based on circulating glucose concentration, as measured by the assessment device 22, in response to neuromodulation. When the concentration is above a predetermined threshold or range, the controller 20 may initiate a treatment protocol of energy application to a region of interest (e.g., liver) and with modulation parameters that are associated with a reduction in circulating glucose. The treatment protocol may use different modulation parameters than those used in the diagnosis protocol (e.g., higher energy levels, more frequent application).

In one embodiment, the memory 132 stores different operating modes that are selectable by the operator. For example, the stored operating modes may include instructions for executing a set of modulation parameters associated with a particular treatment site, such as regions of interest in the liver, pancreas, gastrointestinal tract, spleen. Different sites may have different associated modulation parameters. Rather than having the operator manually input the modes, the controller 20 may be configured to execute the appropriate instruction based on the selection. In another embodiment, the memory 132 stores operating modes for different types of procedures. For example, activation may be associated with a different stimulating pressure or frequency range relative to those associated with depressing or blocking tissue function.

In a specific example, when the energy application device 12 is an ultrasound transducer, the effective amount of energy may involve predetermined temporal average intensity applied to a region of interest. For example, the effective amount of energy may include a time-averaged power (temporal average intensity) and peak positive pressure in the range of 1 mW/cm2-30,000 mW/cm2 (temporal average intensity) and 0.1 MPa to 7 MPa (peak pressure). In one example, the temporal average intensity is less than 35 W/cm2 in the region of interest to avoid levels associated with thermal damage & ablation/cavitation. In another specific example, when the energy application device is a mechanical actuator, the amplitude of vibration is in the range of 0.1 to 10 mm. The selected frequencies may depend on the mode of energy application, e.g., ultrasound or mechanical actuator. The controller 20 may be capable of operating in a validating mode to acquire a treatment position and the treatment position may be implemented as part of a treatment operating mode that is configured to execute a treatment protocol when the energy application device 12 is positioned at the treatment position.

The system may also include an imaging device (e.g., ultrasound imaging probe 28) that facilitates focusing the energy application device 12. In one embodiment, the imaging device may be integrated with or the same device as the energy application device 12 such that different ultrasound parameters (frequency, aperture, or energy) are applied for selecting (e.g., spatially selecting) a region of interest and for focusing energy to the selected region of interest for targeting and subsequently neuromodulation. In another embodiment, the memory 132 stores one or more targeting or focusing modes that is used to spatially select the region of interest within an organ or tissue structure. Spatial selection may include selecting a subregion of an organ to identify a volume of the organ that corresponds to a region of interest. Spatial selection may rely on image data as provided herein. Based on the spatial selection, the energy application device 12 may be focused on the selected volume corresponding to the region of interest. For example, the energy application device 12 may be configured to first operate in the validating mode to acquire the treatment position by capturing image data to be used for identifying the treatment position associated with capturing the region of interest. The validating mode energy is not at levels and/or applied with modulation parameters suitable for neuromodulating treatment. However, once the region of interest is identified, the controller 20 may then operate in a treatment mode according to the modulation parameters associated with achieving targeted physiological outcomes.

The controller 20 may also be configured to receive inputs related to the targeted physiological outcomes as an input to the selection of the modulation parameters. For example, when an imaging modality is used to assess a tissue characteristic, the controller 20 may be configured to receive a calculated index or parameter of the characteristic. Based on whether the index or parameter is above or below a predefined threshold, a diagnosis may be made, and an indication of the diagnosis may be provided (e.g., via a display). In one embodiment, the parameter can be a measure of tissue displacement of the affected tissue or a measure of depth of the affected tissue. Other parameters may include assessing a concentration of one or more molecules of interest (e.g., assessing one or more of a change in concentration relative to a threshold or a baseline/control, a rate of change, determining whether concentration is within a desired range). Further, the energy application device 12 (e.g., an ultrasound transducer) may operate under control of the controller 20 to a) acquire image data of a tissue that may be used to spatially select a region of interest within the target tissue b) apply the modulating energy to the region of interest and c) acquire image to determine that the targeted physiological outcome has occurred (e.g., via displacement measurement). In such an embodiment, the imaging device, the assessment device 22 and the energy application device 12 may be the same device.

The desired target tissue that includes the region of interest 18 (see FIG. 1) may be an internal tissue or an organ that includes synapses of axon terminals and non-neuronal cells. The synapses may be stimulated by direct application of energy to the axon terminals within a field of focus or focal zone of the ultrasound treatment transducer 95 focused on a region of interest 18 of the target tissue to cause release of molecules into the synaptic space, e.g., the release of neurotransmitters and/or the change in ion channel activity in turn causes downstream effects. The region of interest 18 may be selected to include a certain type of axon terminal, such as an axon terminal of a particular neuron type and/or one that forms a synapse with a certain type of non-neuronal cell. Accordingly, the region of interest 18 may be selected to correspond to a portion of the target tissue with the desired axon terminals (and associated non-neuronal cells). The energy application may be selected to preferentially trigger a release of one or more molecules such as neurotransmitters from the nerve within the synapse or directly activate the non-neuronal cell itself through direct energy transduction (i.e. mechanotransduction or voltage-activated proteins within the non-neuronal cells), or cause an activation within both the neural and non-neuronal cells that elicits a desired physiological effect. The region of interest 18 may be selected as the site of nerve entry into the organ. In one embodiment, liver stimulation or modulation may refer to a modulation of the region of interest 18 at or adjacent to the porta hepatis. Acquisition of the treatment position 50 may include selection of the region of interest 18, whereby the position on the patient's body at which the region of interest 18 is within the focal zone of the energy application device 12 when in operation is the treatment position 50.

The energy may be focused or substantially concentrated on a region of interest 18 and to only part of the internal tissue, e.g., less than about 50%, 25%, 10%, or 5% of the total volume of the tissue. That is, the region of interest 18 may be a sub-region of the internal tissue. In one embodiment, energy may be applied to two or more regions of interest 18 in the target tissue, and the total volume of the two or more regions of interest 18 may be less than about 90%, 50%, 25%, 10%, or 5% of the total volume of the tissue. In one embodiment, the energy is applied to only about 1%-50% of the total volume of the tissue, to only about 1%-25% of the total volume of the tissue, to only about 1%-10% of the total volume of the tissue, or to only about 1%-5% of the total volume of the tissue. In certain embodiments, only axon terminal in the region of interest 18 of the target tissue would directly receive the applied energy and release neurotransmitters while the unstimulated axon terminals outside of the region of interest 18 do not receive substantial energy and, therefore, are not activated/stimulated in the same manner. In some embodiments, axon terminals in the portions of the tissue directly receiving the energy would induce an altered neurotransmitter release. In this manner, tissue subregions may be targeted for neuromodulation in a granular manner, e.g., one or more subregions may be selected. In some embodiments, the energy application parameters may be chosen to induce preferential activation of either neural or non-neuronal components within the tissue directly receiving energy to induce a desired combined physiological effect. In certain embodiments, the energy may be focused or concentrated within a volume of less than about 25 mm$^3$. In certain embodiments, the energy may be focused or concentrated within a volume of about 0.5 mm$^3$-50 mm$^3$. However, other focal volumes are also contemplated based on desired physiological outcomes. A focal volume and a focal depth for focusing or concentrating the energy within the region of interest 18 may be influenced by the size/configuration of the energy application device 12. The focal volume of the energy application may be defined by the field of focus or focal zone of the energy application device 12.

As provided herein, the energy may be substantially applied only to the region or regions of interest 18 to preferentially activate the synapse in a targeted manner to achieve targeted physiological outcomes. Accordingly, in certain embodiments, only a subset of a plurality of different types of axon terminals in the tissue is exposed to the direct energy application.

In certain embodiments, the target tissues that include the region of interest 18 are internal tissues or organs that include peripheral nerve endings or peripheral axon terminals. Contemplated tissue targets include gastrointestinal (GI) tissue (stomach, intestines), muscle tissue (cardiac, smooth and skeletal), epithelial tissue (epidermal, organ/GI lining), connective tissue, glandular tissues (exocrine/endocrine), etc. In one example, focused application of energy at a neuromuscular junction facilitates neurotransmitter release at the neuromuscular junction without an upstream action potential. In one embodiment, contemplated targets for modulation may include portions of a pancreas responsible for controlling insulin release or portions of the liver responsible for sensing glucose/metabolites and/or regulating their circulating concentrations.

While certain embodiments are disclosed in the context of ultrasound energy application, it should be understood that other energy types are contemplated, e.g., mechanical energy. Accordingly, the energy application device 12 may be configured as a mechanical vibrator to apply neuromodulating energy. Further, while certain embodiments of the disclosure are discussed in the context of ultrasound imaging data, the system 10 may be implemented to acquire alternative or additional types of imaging data to guide energy application to the region of interest 18.

This written description uses examples to disclose certain embodiments, including the best mode, and also to enable any person skilled in the art to practice the disclosed embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method comprising:
    acquiring ultrasound image data of a subject using a first ultrasound probe coupled to a neuromodulation positioning patch, wherein the neuromodulation positioning patch is not adhered to the skin of the subject;
    identifying or verifying a region of interest based on the acquired ultrasound image data;
    determining a treatment position on the skin of the subject based on the region of interest;
    adjusting a position of the neuromodulation positioning patch coupled to the first ultrasound probe based on the determined treatment position;
    positioning the neuromodulation positioning patch on the skin of the subject such that an opening formed in the neuromodulation positioning patch is positioned on or over the treatment position;
    adhering the neuromodulation positioning patch to the skin of the subject via an application layer of the neuromodulation positioning patch such that the neuromodulation positioning patch is secured to the skin of the subject for subsequent treatment sessions; and
    applying neuromodulating ultrasound energy from the first ultrasound probe or a second ultrasound probe through the treatment position toward the region of interest based on a location of the adhered neuromodulation positioning patch, wherein the first ultrasound probe or the second ultrasound probe is positioned at the opening of the adhered neuromodulation positioning patch so as to apply the neuromodulating ultrasound energy toward the region of interest.

2. The method of claim 1, wherein the neuromodulating ultrasound energy is applied using the second ultrasound probe.

3. The method of claim 2, wherein the first ultrasound probe is an ultrasound imaging probe and the second ultrasound probe is an ultrasound therapy probe.

4. The method of claim 2, comprising:
    prior to applying the neuromodulating ultrasound energy, uncoupling the first ultrasound probe from the neuromodulation positioning patch; and
    coupling the second ultrasound probe to the neuromodulation positioning patch to position the second ultrasound probe at the opening on or over the treatment position.

5. The method of claim 4, wherein coupling the second ultrasound probe to the neuromodulation positioning patch comprises coupling mating features of the second ultrasound probe to complementary mating features of a resilient frame of the neuromodulation positioning patch, wherein the resilient frame is positioned about a perimeter of the opening.

6. The method of claim 1, comprising:
    uncoupling the first ultrasound probe or the second ultrasound probe from the adhered neuromodulation positioning patch; and
    after an interval of time, recoupling the first ultrasound probe or the second ultrasound probe to the adhered neuromodulation positioning patch to apply additional neuromodulating ultrasound energy through the treatment position toward the region of interest for a next scheduled dose.

7. The method of claim 1, wherein acquiring the ultrasound image data of the subject comprises coupling the first ultrasound probe to a removable dock of the neuromodulation positioning patch to position an imaging transducer of the first ultrasound probe within both a dock opening and the opening of the neuromodulation positioning patch.

8. The method of claim 7, comprising uncoupling the removable dock from a frame of the neuromodulation positioning patch.

9. The method of claim 8, wherein the frame or the removable dock comprises a mechanical lock that holds a transducer of the first ultrasound probe at a fixed contact pressure against the subject when the mechanical lock is activated.

10. The method of claim 8, wherein the frame or the removable dock comprises a mechanical lock that holds the first ultrasound probe at a fixed orientation relative to the subject and/or relative to the neuromodulation positioning patch when the mechanical lock is activated.

11. The method of claim 1, wherein the application layer comprises an ultrasound gel portion.

12. The method of claim 11, wherein the application layer further comprises an adhesive portion that is configured to adhere the neuromodulation positioning patch to be secured to onto the skin of the subject.

13. The method of claim 1, wherein acquiring the ultrasound image data comprises acquiring a plurality of images, wherein the plurality of images comprises high resolution images, low resolution images, or a combination of both.

14. The method of claim 1, wherein determining the treatment site comprises identifying internal tissues or organs that include peripheral nerve endings or peripheral axon terminals.

15. The method of claim 1, wherein adhering the neuromodulation positioning patch comprises removing release liners covering an adhesive portion of the application layer on the neuromodulation positioning patch, wherein the adhesive portion is configured to adhere the neuromodulation positioning patch to be secured onto the skin of the subject.

* * * * *